United States Patent von Bonin et al.

[11] Patent Number: 5,308,642
[45] Date of Patent: May 3, 1994

[54] PROCESS FOR THE PRODUCTION OF STIFFENING MATERIALS CONTAINING HYDRAULIC BINDERS, IN PARTICULAR PLASTER BANDAGES

[75] Inventors: Wulf von Bonin, Odenthal; Ulrich von Gizycki, Leverkusen, both of Fed. Rep. of Germany

[73] Assignee: Bayer Aktiengesellschaft, Leverkusen, Fed. Rep. of Germany

[21] Appl. No.: 69,642

[22] Filed: May 26, 1993

Related U.S. Application Data

[63] Continuation of Ser. No. 788,628, Nov. 6, 1991, abandoned.

[30] Foreign Application Priority Data

Nov. 14, 1990 [DE] Fed. Rep. of Germany ....... 4036200

[51] Int. Cl.$^5$ .............................................. A01N 1/02
[52] U.S. Cl. .......................................... 427/2; 602/8; 427/397.7
[58] Field of Search ................... 427/2, 397.7; 602/8

[56] References Cited

U.S. PATENT DOCUMENTS

| | | | |
|---|---|---|---|
| 2,655,148 | 10/1953 | Eberl et al. | 128/91 |
| 3,649,319 | 3/1972 | Smith | 106/111 |
| 4,376,171 | 3/1983 | Blount | 521/100 |
| 4,672,956 | 6/1987 | Potter | 128/90 |

FOREIGN PATENT DOCUMENTS

| | | |
|---|---|---|
| 0234403 | 9/1987 | European Pat. Off. |
| 1504972 | 3/1978 | United Kingdom |

*Primary Examiner*—Shrive Beck
*Assistant Examiner*—David M. Maiorana
*Attorney, Agent, or Firm*—Sprung Horn Kramer & Woods

[57] ABSTRACT

An ecologically harmless process for the production of stiffening materials containing hydraulic binders, for example plaster bandages, is characterized in that a hydraulic binder is mixed in pulverulent form with a reactive binder, this mixture is applied to a sheet-like material, the sheet-like material thus coated is rolled up and the setting reaction of the reactive binder is allowed to proceed before, during and/or after the rolling-up.

3 Claims, No Drawings

PROCESS FOR THE PRODUCTION OF STIFFENING MATERIALS CONTAINING HYDRAULIC BINDERS, IN PARTICULAR PLASTER BANDAGES

This application is a continuation of application Ser. No. 788,628, filed Nov. 06, 1991.

Plaster bandages have been known for a long time and are used to a large extent for orthopaedo-medical purposes.

Plaster bandages have previously been usually produced by making dehydrated plaster into a paste using a binder dissolved in methylene chloride, for example based on modified cellulose, and knife-coating a bandage material, for example a cotton fabric, with this paste. The methylene chloride is then removed by evaporation, as a result of which the plaster is bound to the bandage material by means of a binder. The plaster-containing bandage material can then be cut and rolled without the plaster falling off. The plaster-containing bandage material cut into tapes is then rolled relatively loosely onto perforated, tube-like bobbins or mandrels. The plaster bandage thus formed is activated by dipping it into water. This causes water to penetrate the relatively loose roll from the sides, from the lateral surface and via the perforated core tube, the hydrophilically bound plaster forms a plaster paste, then solidifies the bandage after application and produces a so-called plaster cast.

This production process for plaster bandages has the disadvantage that solvents have to be used, in particular halogenated hydrocarbons, which in today's view are at best tolerable in small amounts and whose removal from the waste air is very complicated and expensive.

A similar procedure is used for producing stiffening materials which are suitable for technical applications.

A process for the production of stiffening materials containing hydraulic binders has now been found, which is characterized in that a hydraulic binder is mixed in pulverulent form with a reactive binder, this mixture is applied to a sheet-like material, the sheet-like material thus coated is rolled up into rolls and the setting reaction of the reactive binder is allowed to proceed before, during and/or after rolling up.

Suitable hydraulic binders are in particular those plaster types which are customary for the production of plaster bandages. Partially dehydrated plaster, so-called plaster of Paris, whose setting time is less than 10 minutes, is preferred. However, other hydraulic binders are also suitable, in particular for the production of stiffening materials for technical areas of application. Examples are: calcium sulphate modifications other than plaster of Paris, such as a-calcium sulphate and anhydrite, and also Portland cement, high-alumina cements, aluminosilicate quick-setting cements, Sorell cements, zinc oxide cements, pozzolan cements and other pulverulent materials of cement character which solidify by reaction with water. The hydraulic binders in pulverulent form to be used according to the invention can also be mixtures of two or more components. It is possible to add to the hydraulic binder customary accelerators, for example soluble sulphates, or retarders or rheological standardising agents, for example proteins or cellulose derivatives.

Suitable reactive binders are the wide range of those known reactive binders or binder mixtures which can be applied to the hydraulic binder in liquid form and whose viscosity can then be increased by reacting the components of the mixture or by exposure to heat, air, moisture, light and/or by a chemical reaction with an optionally additionally incorporated reactant, and/or with a catalyst, a free radical former or other initiator, for example as a result of an increase in the molecular weight. This increase in viscosity can take place, at least partly, in the subsequently formed roll or can be completed therein.

Examples of reactive binders are: silicates of the waterglass type which can be applied without the aid of organic solvents, plaster- or cement-binding salts, epoxides, polyepoxides, epoxy curing agent combinations, double bond systems polymerisable by exposure to air, ion formers or free radical formers, for example mono-, di- or polyolefinic monomers, for example of the cyanoacrylate, acrylate, vinyl ester, allyl ester or allyl ether type, of the silane, siloxane or silicone type (see, also German Offenlegungsschrift 2,357,931), of the alkyd resin and reactive alkyl resin thinner type, of the cyanate resin, phenolic resin, formaldehyde resin, methylol, methylol ether type, and of the (poly)isocyanate type which can be made to react with formation of polyurethanes, polyureas, polycarbodiimides and/or polyisocyanurates, possibly with the participation of the moisture present in the roll.

Polycarboxylic acids, alginates, aluminates, cellulose and starch compounds, which, for example, together with calcium ions or aluminum ions from the hydraulic binder, with which they come into contact, undergo precipitation or hardening are also suitable.

The reactive binders used are preferably a combination of one or more polyols and one or more polyisocyanates. Combinations of polyols and polyisocyanates can, if desired, contain further components, preferably those which retard or accelerate the reaction between polyol and polyisocyanate. Accelerating additives are preferred. Such further components can, if desired, be amounts of 0.05 to 3% by weight (relative to the mixture of polyol and polyisocyanate).

Examples of suitable accelerating additives are aminic or organometallic compounds or also others are the compounds known in polyurethane chemistry as being catalytically active.

The components of the reactive binder can be admixed to the pulverulent hydraulic binder in premixed form, separately and simultaneously or in succession.

The reactive binder can be admixed to the hydraulic binder in amounts of, for example, 0.3 to 50% by weight, preferably 5 to 15% by weight. It is advantageous if this mixture of hydraulic binder and reactive binder still retains a pulverulent, sprinklable character. However, it can also have a knife-coatable paste-like consistency.

Furthermore, it is advantageous to apply the freshly produced mixture of hydraulic and reactive binder immediately or within a few hours after production to the sheet-like material. Before application to the sheet-like material, it is possible to add to the mixture of hydraulic and reactive binder or to individual components thereof, if desired, further additives, such as wetting agents, surfactants, flow-improving agents, colorants and/or biocides.

Preferred polyols for the preferred combinations of polyols and polyisocyanates are the linear and branched polyester polyols and polyether polyols which are used industrially in polyurethane chemistry and are preferably liquid at room temperature. Of particular interest are trifunctional and higher-functional types, which can be obtained by an addition reaction of ethylene oxide and/or propylene oxide with tri- and higher-functional initiators, for example with trimethylolpropane, glycerol, pentaerythritol, sorbitol, sugar or sugar mixtures, triethanolamine, ethylenediamine, polyethylenepolyamine, polypropylenepolyamine, ethanolamine and/or diethanolamine and have OH numbers above 5, preferably between 30 and 400, in particular between 150 and 300.

Suitable polyisocyanates are preferably also aliphatic, araliphatic, heterocyclic and aromatic polyisocyanates used industrially in polyurethane chemistry. Preferably, those polyisocyanates are used whose vapour pressure in the range from 10° to 50° C. is very low. In this case, they can handled without risk. Polyisocyanates of this type are preferably polyisocyanates which are liquid at room temperature, such as polymerised, trimerised, biuretised or allophanatised hexamethylene diisocyanate or isophorone diisocyanate reacted with small amounts of water or those types of aromatic polynuclear polyisocyanates, such as are technically accessible by way of phosgenation of aniline/formaldehyde condensation products and hydrogenated forms thereof. Other liquid polyisocyanates are also suitable, including aliphaticaromatic mixed types, for example those based on isophorone diisocyanate or toluylene diisocyanate or, so called isocyanate prepolymers, i.e. isocyanato-containing, preferably liquid, oligomeric reaction products of the polyols with polyisocyanates.

It is advantageous if the components of these reactive binder mixtures of polyol and polyisocyanate are soluble in one another. It is also possible to use polyol mixtures and/or polyisocyanate mixtures.

The stoichiometric ratios of OH to NCO groups in the polyol/polyisocyanate mixtures can vary within wide limits. Preferably, stoichiometric ratios showing deviations of ±50% by weight are maintained. In specific cases, it is also possible to reduce the ratio of the polyisocyanates and polyols used in each case down to 3% by weight of the stoichiometric equivalent amount or even below that amount. Particular preference is given to the use of reactive binders containing 90 to 130% by weight of the stoichiometrically required amount of polyisocyanate components, relative to the polyol component.

These ratios also apply in the case where the reactive combination of liquid binder components is prepared before, during or after addition to the pulverulent hydraulic binder.

Industrially customary powder mixers can be used without difficulties for the mixing with the hydraulic binder, for example, paddle, propeller or planetary mixers.

Suitable sheet-like materials to which the binder mixture is applied are a wide range of flexible, preferably textile, substrates. They can be made of filaments, fibres, wires or films. They are preferably nonwovens, papers, knitted fabrics or woven fabrics or mixed forms thereof.

Preferably, bandage fabrics made of cotton are used, such as are customary for conventional plaster bandage manufacture. However, suitable textile substrates are all of those which have been produced using, for example, glass fibres, carbon fibres, polyaramide fibres, metallic fibres, polyolefin fibres, polyolefin high-module fibres, polyester fibres, polyacrylonitrile fibres, polyamide fibres and fibres made of refined cellulose and fibre mixtures and/or filament mixtures.

For example, 200 to 1000 g, preferably 400 to 800 g, in particular 500 to 700 g, of the mixture of hydraulic and reactive binder can be applied to 1 $m^2$ of the sheet-like material.

The sheet-like material can be cut to size before or after applying the binder mixture or before or after rolling up, for example to give individual bandages.

The preferably pulverulent or optionally paste-like binder mixture can be applied by a reverse or, preferably, by a direct process, for example by spreading, roller application, blowing, knife application, electrostatically or by any other desired process not requiring any solvent.

The binder mixture can form a homogeneous area on the sheet-like material, but it can also have been applied in the form of stripes, dots, interrupted areas or in the form of patterns, for example in order to allow better penetration of the impregnating water or in order to achieve selective stiffening effects.

If desired, a layer of the binder mixture once applied can be made to form inhomogeneous distributions and/or more permeable regions, for example by shaking or vibrating. It is in general advantageous to press the mixture of reactive and hydraulic binder lightly against the sheet-like material.

It is often advantageous to accelerate setting of the reactive binder with the hydraulic binder by addition of heat. Thus, for example, while or after applying the binder mixture to the sheet-like material, it is possible to add heat or cause heat to be formed, for example by heat conduction, radiation, microwaves, heating gases or a combination of such measures. It is in general advantageous to provide the machines and tools used for applying the binder mixture with a non-adhesive finish, for example by coatings made of polyolefins, silicones, perfluoropolyethylenes or by using release films.

If it is desired to accelerate setting of the reactive binder by addition of heat, it is possible, for example, to heat to a temperature of 30° to 90° C., preferably 50° to 80° C. It is often sufficient to maintain this temperature only for a short time, for example for 0.5 to 60 minutes.

Preferably, it is also possible to let the reactive binder complete the reaction without providing any additional heat, for example by rolling the freshly produced bandage immediately into a roll, it being advantageous for the tubular winding mandrel (diameter for example 0.3 to 5, preferably 0.8 to 1.5 cm), as is customary for plaster bandages, to be already perforated and the setting reaction is allowed to proceed in the rolled-up roll. This can also take place in the intended final packaging. The hydraulic binder can be fixed in the roll in such a manner that it does not or only to a tolerable extent trickle out of the roll upon storage, transport and use.

The reactive binder, in particular in the amounts used of below 15% by weight, relative to the total weight of the stiffening material, surprisingly does not impair penetration of the roll and the hydraulic binder by the water to an unacceptable degree, nor does it impair the stiffening reaction of the paste of the hydraulic binder formed with the water, for example plaster paste. Moreover, the bandage roll can be unrolled after wetting with a sufficient amount of water without difficulties, like that of a conventionally produced plaster bandage, in some cases more cleanly and with fewer difficulties, and be used orthopaedically.

A specific embodiment of providing bandage rolls with the binder mixtures to be used according to the invention, which contain a reactive binder and have a pulverulent character, is made possible by virtue of their property to completely harden with time even at room temperature, the flow ability of the mixture decreasing with time in favour of an adhesive modification. This embodiment simplifies the solvent-free production of stiffening materials considerably.

This embodiment can be realised, for example, by sprinkling or incorporating the preferably pulverulent, if appropriate also paste-like, binder mixture during the rolling up of a bandage fabric, immediately after its production, i.e. in the not yet set state, into the roll which is being formed in a defined amount. For example, shaking chutes, sprinkling units and slot nozzles are suitable for this purpose.

In this embodiment, the reactive binder can be introduced, for example, between the already formed roll and the coating-free bandage fabric which runs in and comes to lie thereon upon winding, so that the mixture of hydraulic and reactive binder is squeezed in layers in between the roll and the new fabric layer.

This is achieved without any great difficulties, since the mixture of hydraulic and reactive binder has a certain self-adhesion and is therefore not squeezed out by the fabric pressure but is shaped to give adhering sheet-like units. Density and permeability of these layers thus formed can be controlled by the roll pressure and tensile forces maintained during the winding process.

In this context, it is advantageous that the binder mixture to be used according to the invention no longer tends to dust even in the not-set state. This improves the room air conditions during bandage production considerably.

The rolls thus produced then set in the course of time, it being possible for the setting process to be extended to the final packaging stage. The setting process effectively prevents the hydraulic binder incorporated in the roll from flowing out.

After the setting process, the hydraulic binder is present in the form of more or less finely divided particles bound by the reactive binder. Surprisingly, this structure does not impair setting of the hydraulic binder with water, but in contrast ensures that the water, when the roll is dipped in for, for example 10 to 60 seconds, very rapidly and uniformly penetrates, only a small excess of water, i.e. a limited amount of water, being absorbed by the roll. Furthermore, only a small amount of hydraulic binder is discharged from the roll together with the excess water. This leads to a significant improvement in cleanliness when handling such bandages soaked with water compared with the conventional production of plaster bandages. On the other hand, the grain structure of the binder mixture handled according to the invention does not or only slightly impairs the spreadability and mouldability of the stiffening materials produced according to the invention.

When plaster bandages are prepared according to the invention, the bandages can be cut, rolled up and packaged by the conventional methods of plaster bandage production. The same is also true of the other application methods for stiffening materials produced according to the invention.

Stiffening materials obtainable according to the invention can be used, for example, in the medico-orthopaedic sector, for the production of replicas, masks and moulded articles, for the reinforcement of plastic parts or as protective covering against mechanical and/or thermal influences, for insulations, for fire prevention purposes, for sealing purposes, in joining technology and for the stiffening of structural elements. For these purposes, stiffening materials produced according to the invention, in particular plaster bandages, can be activated in the usual manner by dipping them wound onto suitable, for example perforated, bobbins into water for a short period of time. The dipping time can be, for example, 10 to 60 seconds at a temperature of 0° to 80° C., preferably 15° to 30° C.

The process according to the invention has the advantage that it is dust-free but "dry", i.e. that no solvents are required. Nor is any contaminating waste air produced which could only be purified in a complicated and expensive manner. This constitutes a considerable simplification compared with the prior art.

The process according to the invention is illustrated below by way of example. Parts and percentages are by weight, unless stated otherwise.

EXAMPLES

The following materials were used in the examples: strips, 10 cm wide and 300 cm long, or continuous strips made of cotton fabric, such as usually used for the production of plaster bandages, the weight of the fabric strip being 2.56 g per metre.

Plaster powder, such as is used as so-called hemihydrate or plaster of Paris for the manufacture of plaster bandages by conventional methods.

Polyol A, a technical grade adduct of 80 mol of propylene oxide and 20 mol of ethylene oxide with sorbitol having an OH number of 175.

Polyol B, a technical grade adduct of equal parts of ethyleneoxide and propylene oxide with glycerol having an OH number of 250.

Polyol C, a technical grade adduct of 60% of ethylene oxide and 40% of propylene oxide with sorbitol having an OH number of 8.

Isocyanate A, a technical grade biuretisation product of hexamethylene diisocyanate (Desmoduro ® N, from Bayer AG) having an isocyanate content of 21%.

Isocyanate B, a technical grade polynuclear polyisocyanate from phosgenation of aniline/formaldehyde condensation products having an isocyanate content of 31% (Desmodur ® 44 V, from Bayer AG).

In a high-speed paddle mixer (Lödige mixer), the following binder mixtures, which were all flowable or sprinklable, were prepared at room temperature from the calcium sulphate and the polyols and polyisocyanates:

Mixture 1:
150 parts of plaster powder were initially introduced and a mixture of 10 parts of polyol A and 6.9 parts of polyisocyanate A was added.

Mixture 2:
150 parts of plaster powder were initially introduced and first 6.9 parts of polyisocyanate A and then 10 parts of polyol A were added.

Mixture 3:
150 parts of plaster powder were initially introduced and a mixture of 10 parts of polyol A and 4.6 parts of polyisocyanate B was added.

Mixture 4:
150 parts of plaster powder were initially introduced and first 10 parts of polyol A and then 4.6 parts of polyisocyanate B were added.

Mixture 5:

100 parts of plaster powder were initially introduced and 15 parts of a mixture of 100 parts of polyol C. and 0.2 part of polyisocyanate B was added.

EXAMPLE 1

The cotton fabric was placed on a strip of polyethylene film sprayed with a silicone-based release agent and moved along under a sprinkler in such a manner that 1 $M^2$ of the cotton fabric was in each case coated with 600 g each of a freshly prepared mixture of types 1 to 5 in separate batches.

The layer sprinkled on in each case was lightly pressed down using a roller provided with a non-adhesive surface. The sprinkled cotton fabric was then moved through a heating tunnel, where it was heated at temperatures between 60 and 80° C. (increasing) for one minute.

After leaving the heating tunnel, the cotton fabric now provided with an adhesive binder layer was cut to a length of 3 m, wound onto a tubular, perforated winding mandrel and then melted into a polyethylene-laminated aluminum film in a packaging apparatus, as is also done in the production of plaster bandages by a conventional method, if it is desired to particularly protect it before application.

For application, the rolls were removed from the packaging after 2 weeks. As a result of the complete setting of mixtures 1 to 5 which had taken place in the meantime, the rolls could be handled without any substantial flowing-out of the plaster. They were dipped into water at 18° C. for 30 seconds and somewhat milled manually. A cardboard test specimen, 8 cm in diameter, was then wrapped therewith and levelled. After 4 minutes, the plaster dressing thus produced had stiffened. Hardening behaviour and applicability were approximately those of a 10 cm plaster bandage produced in the usual manner and equipped with 600 g of plaster material per $m^2$, except that the impregnating water and the aqueous phase pressed out during processing had much less the character of plaster liquor but more that of slightly cloudy water and thus allowed substantially cleaner processing than with customary plaster bandages.

EXAMPLE 2

The procedure of Example 1 was repeated, except that 3 parts of dehydrated magnesium sulphate were in each case added to the plaster powder. Due to the accelerating effect of the magnesium sulphate, the rolls hardened in the application test in as little as 2.5 minutes.

EXAMPLE 3

The procedure of Example 1 was repeated, except that 3% by weight (relative to the mixture) of a surfactant comprising an adduct of 40 mol ethylene oxide with 1 mol of abietic acid was added in each case when the mixtures were prepared, in order to increase water wettability. In the application test, dipping into water was only carried out for 16 seconds, leading to analogous processing properties as in Example 1.

EXAMPLE 4

The bandage fabric was attached to a winding mandrel and wound to a roll. During this, the fabric strip to be wound approached the winding mandrel from top to bottom at an angle of 45°. Mixtures 1 to 5 were sprinkled onto the roll being formed in separate batches using a shaking chute, so that the powders were deposited on the surface of the roll and enclosed between freshly running-in fabric and roll as a result of the winding process. The amount of the binder mixture was set to such a value that 600 g of the binder mixtures 1 to 5 were deposited per $m^2$ of bandage fabric in the roll.

The rolls were then cut to a length of 3 m and wrapped in a paper envelope. After 24 to 60 hours, the setting process was complete and almost no binder flowed out of the roll when the packaging was opened.

The application test took an analogous course to Example 1.

EXAMPLE 5

The same experiment (Example 4) was repeated, except that a mixture of equal parts of α-calcium sulphate and Portland cement was used as hydraulic binder and mixture 1 and mixture 2 were used as reactive binder. This binder mixture hardened virtually free of expansion and shrinkage.

EXAMPLE 6

The procedure of Example 4 was repeated, except that a glass fabric strip, 10 cm wide and having a weight of 5.9 g per metre was used as fabric strip. In the application test, the behaviour found was analogous to that of Example 1.

EXAMPLE 7

The procedure of Example 1 was repeated, except that a polyester yarn fabric strip was used (so-called raschelknitted fabric), which had good transverse stretchability and a weight of 3.35 g per meter. In the application test, the behaviour found was analogous to that in Example 1.

What is claimed is:

1. A process for the production of stiffening materials containing hydraulic binders, in which:
    a hydraulic binder is mixed in pulverulent form with a reactive binder, said reactive binder being a combination of one or more polyols and one or more polyisocyanates;
    this mixture is applied to a flexible substrate; and
    the reactive binder is then reacted to bind the hydraulic binder, in an unreacted state, to the flexible substrate whereby, when subsequently exposed to water, the water can penetrate the reacted binder to react and wet the hydraulic bind, and can cause the hydraulic binder to set and form a stiff material.

2. The process of claim 1, in which the mixture of hydraulic binder and reactive binder has a pulverulent, sprinklable character.

3. The process of claim 1, in which the ratio of OH to NCO groups in polyol/polyisocyanate mixtures deviates by up to ± 50% by weight from the stoichiometrically required ratio.

* * * * *